United States Patent

Messerges

(10) Patent No.: US 8,978,651 B2
(45) Date of Patent: Mar. 17, 2015

(54) ANESTHESIA SYSTEM AND METHOD

(75) Inventor: Joanne Lynn Messerges, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 1602 days.

(21) Appl. No.: 12/259,678

(22) Filed: Oct. 28, 2008

(65) Prior Publication Data

US 2010/0101571 A1 Apr. 29, 2010

(51) Int. Cl.
*A61M 16/01* (2006.01)
*A61M 16/10* (2006.01)
*A61M 16/12* (2006.01)
*A61M 16/18* (2006.01)

(52) U.S. Cl.
CPC ............. *A61M 16/12* (2013.01); *A61M 16/104* (2013.01); *A61M 16/18* (2013.01); *A61M 2016/1035* (2013.01); *A61M 2202/0208* (2013.01); *A61M 2202/0283* (2013.01); *A61M 2205/3331* (2013.01); *A61M 2205/502* (2013.01); *A61M 2230/437* (2013.01)
USPC .................................. 128/204.22; 128/203.12

(58) Field of Classification Search
CPC ............. A61M 16/00; A61M 16/0003; A61M 16/0051; A61M 16/01; A61M 16/04; A61M 16/22; A61M 2016/1035
USPC ............. 128/200.24, 203.12, 203.13, 203.14, 128/203.25, 204.18, 204.21, 204.22
See application file for complete search history.

(56) References Cited

U.S. PATENT DOCUMENTS

| | | | | |
|---|---|---|---|---|
| 4,905,685 A | * | 3/1990 | Olsson et al. ............. | 128/203.12 |
| 6,216,690 B1 | * | 4/2001 | Keitel et al. .............. | 128/203.12 |
| 6,539,311 B1 | * | 3/2003 | Berger ........................... | 702/23 |
| 7,681,574 B2 | * | 3/2010 | Heinonen ................. | 128/204.21 |
| 2006/0081244 A1 | * | 4/2006 | Bouillon et al. ......... | 128/200.24 |
| 2006/0090757 A1 | * | 5/2006 | Dittmann ................. | 128/203.12 |
| 2007/0167853 A1 | * | 7/2007 | Melker et al. ................. | 600/532 |

OTHER PUBLICATIONS http://bja.oxfordjournals.org/cgi/content/abstract/86/1/12.
http://www.anesthesia-analgesia.org/cgi/content/abstract/95/6/1616?ck=nck.
Carpenter, Randall L. et al; Pharmacokinetic of Inhaled Anesthetics in Humans: Measurements during and after the Simultaneous Administration of Enflurane, Halothane, Isoflurane, Methoxyflurane, and Nitrous Oxide; Anesth. Analg. vol. 65, 1986, pp. 575-582.
http://bja.oxfordjournals.org/cgi/content/abstract/86/1/12, 2001.
http://www.anesthesia-analgesia.org/cgi/content/abstract/95/6/1616?ck=nck, 2002.

* cited by examiner

*Primary Examiner* — Valerie L Skorupa
(74) *Attorney, Agent, or Firm* — Andrus Intellectual Property Law, LLP

(57) ABSTRACT

An anesthesia system is disclosed herein. The anesthesia system includes a sensor configured to measure an anesthetic agent concentration, and a processor connected to the sensor. The processor is configured to generate an exponential agent model based on the measured anesthetic agent concentration. The exponential agent model represents a plurality of future anesthetic agent concentrations.

17 Claims, 2 Drawing Sheets

ANESTHESIA SYSTEM AND METHOD

FIELD OF THE INVENTION

The subject matter disclosed herein relates to an anesthesia system and method.

BACKGROUND OF THE INVENTION

Anesthesia systems may be implemented for purposes such as blocking the conscious perception of pain, producing unconsciousness, preventing memory formation, and/or preventing unwanted movement. Anesthesia systems configured to administer an inhaled anesthetic agent generally comprise a vaporizer adapted to convert the inhaled anesthetic agent into a gas, and a ventilator adapted to mechanically move breathable gasses into and out of the lungs.

The anesthetic agent inhaled into the patient's lungs is not immediately absorbed. Instead, the anesthetic agent concentrations take time to reach equilibrium within the breathing circuit and within the patient. A clinician must choose vaporizer and ventilator settings in a manner adapted to produce a future clinical effect such as unconsciousness. One problem is that it is difficult to estimate the time at which the future clinical effect will take place. Another problem is that it is difficult to select the vaporizer and ventilator settings that produce the future clinical effect in an optimal manner. For example, it is difficult to select vaporizer and ventilator settings adapted to safely and efficiently cause unconsciousness.

BRIEF DESCRIPTION OF THE INVENTION

The above-mentioned shortcomings, disadvantages and problems are addressed herein which will be understood by reading and understanding the following specification.

In an embodiment, an anesthesia system includes a sensor configured to measure an anesthetic agent concentration, and a processor connected to the sensor. The processor is configured to generate an exponential agent model based on the measured anesthetic agent concentration. The exponential agent model represents a plurality of future anesthetic agent concentrations.

In another embodiment, an anesthesia system includes a vaporizer, a breathing circuit pneumatically coupled with the vaporizer, and a sensor disposed within the breathing circuit. The sensor is configured to measure a plurality of anesthetic agent concentrations. The anesthesia system also includes a processor connected to the sensor and the vaporizer. The processor is configured to generate an exponential agent model based on the plurality of anesthetic agent concentrations and vaporizer setting data from the vaporizer. The exponential agent model represents a plurality of future anesthetic agent concentrations.

In another embodiment, a method includes providing an anesthesia system comprising a sensor and a processor operatively connected to the sensor, implementing the sensor to measure a plurality of anesthetic agent concentrations, and implementing the processor to generate an exponential agent model based on the plurality of anesthetic agent concentrations. The exponential agent model represents a plurality of future anesthetic agent concentrations.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
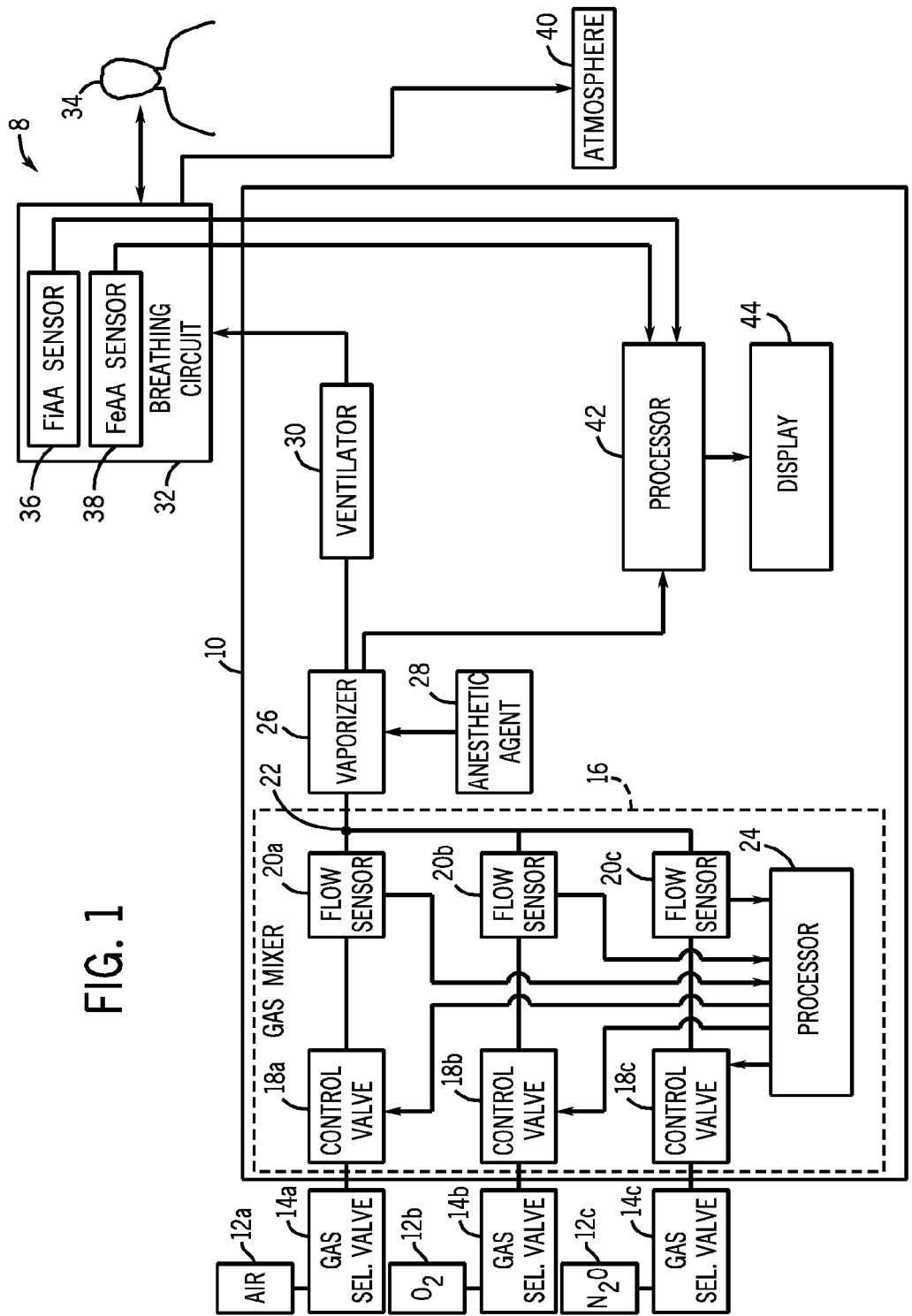
FIG. 1 is a schematic diagram illustrating an anesthesia system connected to a patient in accordance with an embodiment.

Referring to FIG. 1, an anesthesia system 8 is schematically depicted in accordance with an embodiment. The anesthesia system 8 includes an anesthesia machine 10, a plurality of gas storage devices 12a, 12b and 12c, and a breathing circuit 32. The anesthesia machine 10 is shown for illustrative purposes and it should be appreciated that other types of anesthesia machines may alternately be implemented. In a typical hospital environment, the gas storage devices 12a, 12b and 12c are centrally located storage tanks configured to supply medical gas to multiple anesthesia machines. The storage tanks are generally pressurized to facilitate the transfer of the medical gas to the anesthesia machine 10.

The gas storage devices 12a, 12b and 12c will hereinafter be described as including an air tank 12a, an oxygen ($O_2$) tank 12b, and a nitrous oxide ($N_2O$) tank 12c, respectively, however it should be appreciated that other storage devices and other types of gas may alternatively be implemented. The gas storage tanks 12a, 12b and 12c are each connected to one of the gas selector valves 14a, 14b, and 14c, respectively. The gas selector valves 14a, 14b and 14c may be implemented to shut off the flow of medical gas from the storage tanks 12a, 12b and 12c when the anesthesia machine 10 is not operational. When one of the gas selector valves 14a, 14b and 14c is opened, gas from a respective storage tank 12a, 12b and 12c is transferred under pressure to the anesthesia machine 10.

The anesthesia machine 10 includes a gas mixer 16 adapted to receive medical gas from the storage tanks 12a, 12b and 12c. The gas mixer 16 includes a plurality of control valves 18a, 18b and 18c that are respectively connected to one of the gas selector valves 14a, 14b and 14c. The gas mixer 16 also includes a plurality of flow sensors 20a, 20b and 20c that are each disposed downstream from a respective control valve 18a, 18b, and 18c. After passing through one of the control valves 18a, 18b and 18c, and passing by one of the flow sensors 20a, 20b and 20c, the individual gasses (i.e., air, $O_2$ and $N_2O$) are combined to form a mixed gas at the mixed gas outlet 22.

The control valves 18a, 18b and 18c and the flow sensors 20a, 20b and 20c are each connected to a processor 24. The processor 24 is configured to operate the control valves 18a, 18b and 18c in a response to gas flow rate feedback from the sensors 20a, 20b and 20c. Accordingly, the processor 24 can be implemented to maintain a selectable flow rate for each gas (i.e., air, $O_2$ and $N_2O$) such that the mixed gas at the mixed gas outlet 22 comprises a selectable ratio of air, $O_2$ and $N_2O$. The mixed gas flows to a vaporizer 26 where an anesthetic agent 28 is vaporized and added to the mixed gas from the mixed gas outlet 22. The vaporized anesthetic agent 28 and mixed gas combination passes through a ventilator 30, enters the breathing circuit 32 and is delivered to the patient 34. After being delivered to the patient 34, a portion of the vaporized anesthetic agent 28 and mixed gas combination is absorbed by the patient's lungs (not shown) and the remainder is vented to atmosphere 40 or recycled in a conventional manner. The ventilator 30 is implemented to mechanically move the vaporized anesthetic agent 28 and mixed gas combination into and out of the patient's lungs.

A fractional inspired anesthetic agent (FiAA) sensor 36 and a fractional expired anesthetic agent (FeAA) sensor 38 may be disposed within the breathing circuit 32. The FiAA sensor 36 and the FeAA sensor 38 are respectively configured to measure the concentration of anesthetic agent inhaled by and exhaled from the patient 34. The FiAA sensor 36 and the FeAA sensor 38 may be operatively connected to a processor 42. The processor 42 may also be operatively connected to the vaporizer 26 and a display 44.

According to one embodiment, the processor 42 is configured to generate a model 60 (shown in FIG. 2) representing a plurality of future expired anesthetic agent concentrations. Research has shown that expired anesthetic agent concentrations generally increase or decrease in an exponential manner. Accordingly, the model 60 is based on an exponential equation and will hereinafter be referred to as the exponential expired agent model 60. The processor 42 may generate the exponential expired agent model 60 based on data from the FeAA sensor 38 and/or the vaporizer 26. The display 44 may be configured to visually convey the exponential expired agent model 60. Although the processor 42 is described in accordance with an exemplary embodiment as being configured to generate an expired agent model based on data form the FeAA sensor 38, it should be appreciated that alternate embodiments may comprise the generation of other exponential anesthetic agent models (e.g., an inspired agent model) based on other types of data (e.g., data from the FiAA sensor 36).

A clinician may implement the exponential expired agent model 60 (shown in FIG. 2) to estimate the time at which the future clinical effect will take place. For example, the clinician may implement the exponential expired agent model 60 to estimate the time required for a patient to become unconscious. The clinician may also implement the exponential expired agent model 60 to select the vaporizer and/or ventilator settings that produce a future clinical effect in an optimal manner. For example, the clinician may implement the exponential expired agent model 60 to select vaporizer and/or ventilator settings adapted to safely and efficiently render the patient unconscious.

It should be appreciated that the processor 42 may be configured to derive the exponential expired agent model 60 (shown in FIG. 2) in a number of different ways. The following disclosure will describe one such method for generating the exponential expired agent model 60. For purposes of more clearly illustrating this method, assume that the three immediately preceding measured expired agent values A(t) acquired at times $t_{-2}$, $t_{-1}$ and $t_0$ from the FeAA sensor 38 respectively comprise concentrations of 1.2 volume per volume (v per v), 1.5 v per v, and 1.7 v per v. Additionally assume that patient 34 is being anesthetized with the anesthetic agent Sevoflurane.

The exponential expired agent model 60 (shown in FIG. 2) may be derived using the exponential equation $A'(t)=A^{\infty}-(A^{\infty}-A^{0})e^{-\tau}$. The variable $A'(t)$ represents the predicted expired agent value at time t. The variable $A^{\infty}$ represents the expired agent asymptotic value. As will be appreciated by those skilled in the art, the expired agent asymptotic value is the expired agent value approached as time t approaches infinity ($\infty$). The variable $A^0$ represents the initial expired agent value. The variable $\tau$ represents the exponential time constant, and the variable t represents the time.

According to one embodiment, the unknown variables $A^{\infty}$, $A^0$, and $\tau$ from the previously described exponential equation can be solved for using the measured expired agent values A(t) acquired at times $t_{-2}$, $t_{-1}$ and $t_0$ from the FeAA sensor 38, and vaporizer setting data from the vaporizer 26. Variable $A^0$ is set equal to the measured expired agent value A(t) acquired at time $t_{-2}$, which in the current exemplary embodiment is assumed to be 1.2 v per v.

Variables $A^{\infty}$ and $\tau$ may be estimated by identifying the values of $A^{\infty}$ and $\tau$ that produce the least error between the predicted values $A'(t)$ and the measured values A(t) for times $t_{-2}$, $t_{-1}$, and $t_0$. One way to identify the variable values that minimize this error is to establish bounds that limit the scope of the search, and then to try each value within the bounds in order to see which produce the least error. The bounds for the search may be established based on physiological and anesthesia principles. According to one embodiment, the bounds for the search are established in part based on vaporizer setting data from the vaporizer 26. Referring again to the exemplary embodiment and solving for the variables $A^{\infty}$ and $\tau$ in the manner described yields the following results: $A^{\infty}=1.749$, and $\tau=0.0185$.

Figure 2:
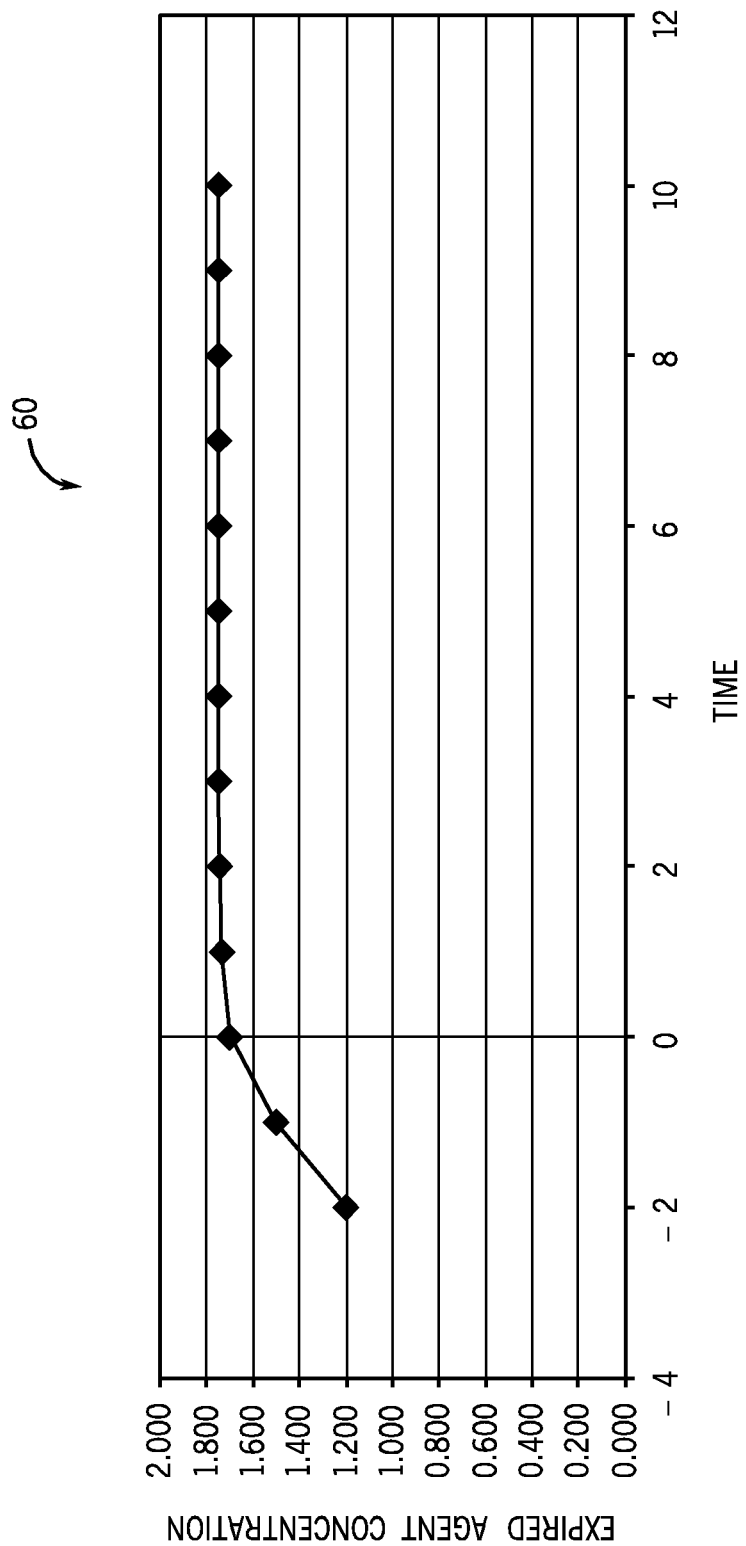
FIG. 2 is a plot illustrating an exponential expired agent model in accordance with an embodiment.

Referring to FIG. 2, the exponential agent model 60 based on the equation $A'(t)=A^{\infty}-(A^{\infty}-A^{0})e^{-\tau}$ and solved in the manner previously described allows a user to estimate future expired agent concentrations. As shown in FIG. 2, at a future time $t_1$ the estimated expired agent concentration is 1.733 v per v; at a future time $t_2$ the estimated expired agent concentration is 1.743 v per v; and at a future time $t_3$ the estimated expired agent concentration is 1.747 v per v. At the future times $t_4$-$t_5$ the estimated expired agent concentration is 1.747 v per v; and at the future times $t_6$-$t_{10}$ the estimated expired agent concentration is 1.748 v per v.

It should be appreciated that the future expired agent concentrations from the model 60 can be implemented to estimate future plasma concentrations in the patient's lungs in a known manner such as, for example, based on the patient's physical characteristics. For purposes of this disclosure, a plasma concentration refers to the concentration of anesthetic agent in a given plasma sample. The future plasma concentrations in the patient's lungs can further be implemented to estimate future plasma concentrations in the patient's brain in a known manner. It will be appreciated by those skilled in the art that future plasma concentrations in the patient's brain can be implemented to predict future clinical effects such as unconsciousness.

According to one embodiment, the exponential expired agent model 60 and/or any plasma concentrations derived therefrom can be visually conveyed to a clinician via the display 44 (shown in FIG. 1). This information may, for example, be implemented in order to estimate the time at which a future clinical effect will take place, or to select optimal anesthesia machine 10 settings.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

I claim:

1. An anesthesia system comprising:
a breathing circuit configured to deliver medical gas and anesthetic agent to a patient;
a sensor that measures an anesthetic agent concentration in the breathing circuit: and
a processor connected to the sensor, said processor receives the measured anesthetic agent concentration and generates an exponential agent model based on the measured anesthetic agent concentration, said exponential agent model representing a plurality of future anesthetic agent concentrations expired by the patient.

2. The anesthesia system of claim 1, wherein the sensor is configured to measure one of an inspired anesthetic agent concentration and an expired anesthetic agent concentration.

3. The anesthesia system of claim 1, wherein the processor estimates a plasma concentration based on the exponential agent model.

4. The anesthesia system of claim 1, further comprising a vaporizer operatively connected to the processor.

5. The anesthesia system of claim 4, wherein the processor is configured to generate the exponential agent model based on vaporizer setting data from the vaporizer.

6. The anesthesia system of claim 1, wherein the sensor is at least partially disposed within a breathing circuit.

7. The anesthesia system of claim 6. further comprising a ventilator pneumatically coupled with the breathing circuit.

8. The anesthesia system of claim 1, further comprising a display operatively connected to the processor, said display configured to visually convey the plurality of future expired anesthetic agent concentrations.

9. A method comprising:
providing an anesthesia system comprising a sensor and a processor operatively connected to the sensor:
implementing the sensor to measure a plurality of exhaled anesthetic agent concentrations in the anesthesia. system; and
implementing the processor to generate an exponential agent model based on the plurality of measured exhaled anesthetic agent concentrations, said exponential agent model representing a plurality of future anesthetic agent concentrations expired by a patient.

10. The method of claim 9, further comprising estimating a plasma concentration based on the exponential agent model.

11. The method of claim 9, wherein said implementing the processor to generate an exponential agent model comprises implementing the processor to generate the exponential agent model further based on vaporizer setting data.

12. The method of claim 9, further comprising; visually conveying information derived from the exponential agent model.

13. A method comprising:
providing an anesthesia system comprising, a sensor and a processor operatively connected to the sensor;
measuring a plurality of sequential anesthetic agent concentrations, exhaled by the patient into the anesthesia system;
generating, with the processor, an exponential expired agent model by fitting the exponential expired agent model to the plurality of measured anesthetic agent concentrations exhaled by the patient;
estimating, with the processor, a future anesthetic agent concentration exhaled by the patient; and
estimating, with the processor, a future plasma concentration of anesthetic agent from the estimated future anesthetic agent concentration exhaled by the patient.

14. The method of claim 13, wherein the estimated future plasma concentration is an estimated future plasma concentration in the lungs.

15. The method of claim 13, wherein the estimated future plasma concentration is a future plasma concentration in the brain of the patient.

16. The method of dam 13, wherein the estimated future plasma concentration is an estimated future plasma concentration in the lungs of the patient and further comprising:
estimating, with the processor, a future plasma concentration in the brain of the patient from the estimated future plasma concentration in the lungs of the patient.

17. A method comprising:
providing an anesthesia system comprising a sensor and a processor operatively connected to the sensor;
implementing the sensor to measure a plurality of exhaled anesthetic agent concentrations in the anesthesia system;
implementing the processor to generate an exponential agent model based on the plurality of measured exhaled anesthetic agent concentrations, said exponential agent model representing a plurality of future anesthetic agent concentrations expired by a patient;
minimizing an error between an estimated exhaled. agent concentration and measured exhaled agent concentrations; and
estimating an expired agent asymptotic value and an exhaled agent time constant;
wherein the future anesthetic agent concentrations are based upon the estimated exhaled agent asymptotic. value, estimated expired agent time constant, and the plurality of measured exhaled anesthetic agent concentrations.

* * * * *